United States Patent
Rhoads et al.

(10) Patent No.: US 11,782,007 B2
(45) Date of Patent: Oct. 10, 2023

(54) $CO_2$ SENSOR BASED ON CARBON NANOTUBE-FUNCTIONAL POLYMER COMPOSITE FILMS

(71) Applicant: Purdue Research Foundation, West Lafayette, IN (US)

(72) Inventors: Jeffrey Frederick Rhoads, West Lafayette, IN (US); George Tsu-Chih Chiu, West Lafayette, IN (US); Bryan W Boudouris, West Lafayette, IN (US); Nikhil Bajaj, West Lafayette, IN (US); Allison Kelly Murray, West Lafayette, IN (US); Zachary A Siefker, West Lafayette, IN (US); Xikang Zhao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 430 days.

(21) Appl. No.: 16/986,340

(22) Filed: Aug. 6, 2020

(65) Prior Publication Data
US 2021/0041387 A1   Feb. 11, 2021

Related U.S. Application Data

(60) Provisional application No. 62/884,390, filed on Aug. 8, 2019.

(51) Int. Cl.
*G01N 27/12* (2006.01)
*B32B 9/00* (2006.01)
(Continued)

(52) U.S. Cl.
CPC .......... *G01N 27/127* (2013.01); *B32B 9/007* (2013.01); *B32B 9/045* (2013.01); *B32B 27/302* (2013.01);
(Continued)

(58) Field of Classification Search
None
See application file for complete search history.

(56) References Cited

U.S. PATENT DOCUMENTS

2009/0266230 A1* 10/2009 Radosz ................. B01J 20/264
528/289

FOREIGN PATENT DOCUMENTS

| KR | 2017044529 A * | 4/2017 | ......... C01B 31/0438 |
| WO | 2016010855 A1 | 1/2016 | |
| WO | 2018216017 A1 | 11/2018 | |

OTHER PUBLICATIONS

Ren et al., "Facile strategy for preparation of core-shell-structured carbon nanotube-ionic liquid hybrids," Material Letters, vol. 166, pp. 133-135 (2016). (Year: 2016).*

(Continued)

*Primary Examiner* — Randy P Gulakowski
*Assistant Examiner* — Ha S Nguyen
(74) *Attorney, Agent, or Firm* — Purdue Research Foundation

(57) ABSTRACT

The present disclosure relates to a novel composite film configured for $CO_2$ sensing, and the method of making and using the novel composite film. The novel composite film comprises a carbon nanotube film and a $CO_2$ absorbing layer deposited on the carbon nanotube film, wherein the $CO_2$ (Continued)

absorbing layer comprises a mixture of a branched polyethylenimine, a polyethylene glycol, and poly[1-(4-vinylbenzyl)-3-methylimidazolium tetrafluoroborate] of formula I:

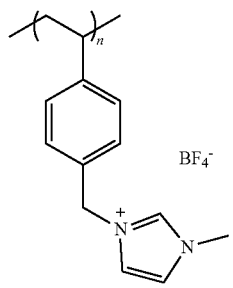

wherein n ranges from 10-300.

7 Claims, 3 Drawing Sheets

(51) Int. Cl.
| | |
|---|---|
| *B32B 9/04* | (2006.01) |
| *B32B 27/30* | (2006.01) |
| *C01B 32/174* | (2017.01) |
| *C08G 73/02* | (2006.01) |
| *C08L 71/02* | (2006.01) |
| *C08L 79/02* | (2006.01) |
| *B82Y 15/00* | (2011.01) |
| *B82Y 30/00* | (2011.01) |
| *G01N 33/00* | (2006.01) |
| *C08L 39/04* | (2006.01) |

(52) U.S. Cl.
CPC ........ *C01B 32/174* (2017.08); *C08G 73/0206* (2013.01); *C08L 71/02* (2013.01); *C08L 79/02* (2013.01); *G01N 27/126* (2013.01); *B82Y 15/00* (2013.01); *B82Y 30/00* (2013.01); *G01N 33/004* (2013.01)

(56) References Cited

OTHER PUBLICATIONS

Li et al., "Poly(ionic liquid)-wrapped single-walled carbon nanotubes forsub-ppb detection of CO2," Chem. Commun. vol. 48, pp. 8222-8224 (2012) (Year: 2012).*
Weekly K. et al., Modeling and estimation of the humans' effect on the CO2 dynamics inside a conference room, IEEE Transactions on Control Systems Technology, vol. 23, No. 5, pp. 1770-1781, 2015.
Willa K. et al., When Nanoparticles Meet Poly(Ionic Liquid)s: Chemoresistive CO 2 Sensing at Room Temperature, Adv. Funct. Mater. 2015, 25, 2537-2542.

* cited by examiner

CO₂ SENSOR BASED ON CARBON NANOTUBE-FUNCTIONAL POLYMER COMPOSITE FILMS

CROSS-REFERENCE TO RELATED APPLICATION

This application claims the priority benefit of U.S. Provisional Patent application No. 62/884,390, filed Aug. 8, 2019, the contents of which is incorporated herein by reference in its entirety.

GOVERNMENT RIGHTS

This invention was made with government support under DE-AR0000943 awarded by the Department of Energy. The government has certain rights in the invention.

TECHNICAL FIELD

The present disclosure relates to a novel composite film configured for $CO_2$ sensing, and the method of making and using the novel composite film.

BACKGROUND

This section introduces aspects that may help facilitate a better understanding of the disclosure. Accordingly, these statements are to be read in this light and are not to be understood as admissions about what is or is not prior art.

Carbon dioxide ($CO_2$) gas levels are commonly monitored within the context of building heating, ventilation, and air conditioning (HVAC) systems as one measure of indoor air quality. While reliable $CO_2$ sensing is valuable in this and several other laboratory and industrial applications, few commercial $CO_2$ sensors demonstrate long term reliability in conjunction with low cost and low power consumption. The state-of-the-art application of commercial $CO_2$ sensors is perhaps best defined by works such as Weekly, et al., which highlights the clear, measurable relationship between $CO_2$ concentrations in indoor spaces and occupancy through the use of off-the-shelf hardware. See K. Weekly, et al., "Modeling and estimation of the humans' effect on the $CO_2$ dynamics inside a conference room," *IEEE Transactions on Control Systems Technology*, vol. 23, no. 5, pp. 1770-1781, 2015. Unfortunately, the nondis-persive infrared (NDIR) sensor used in that work exhibited a repeatability of ±20 ppm and a warm up time on the order of 10 min. Additionally, NDIR sensor power consumption is often on the order of 200 mW, making battery-powered, wirelessly deployed operation challenging. Such sensors are also outside of the range of power consumption generally considered viable for long-term energy harvesting using, for example, indoor photovoltaic cells. Other notable methods reported in the literature for sensing $CO_2$ include resonant sensing via microelectromechanical systems (MEMS) and photoacoustic methods.

Therefore, there is a need for low-cost and low-power sensing materials, devices and methods.

SUMMARY

The present disclosure relates to a novel composite film configured for $CO_2$ sensing, and the method of making and using the novel composite film.

In one embodiment, the present disclosure provides a composite film configured for $CO_2$ sensing, wherein the composite film comprises a carbon nanotube film and a $CO_2$ absorbing layer deposited on the carbon nanotube film, wherein the $CO_2$ absorbing layer comprises a mixture of a branched polyethylenimine, a polyethylene glycol, and poly[1-(4-vinylbenzyl)-3-methylimidazolium tetrafluoroborate] (PVBMIBF4) of formula I:

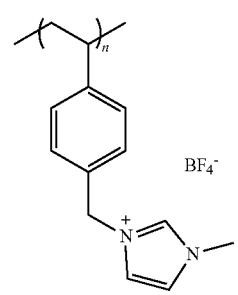

wherein n ranges from 10-300.

DETAILED DESCRIPTION

Figure 1:
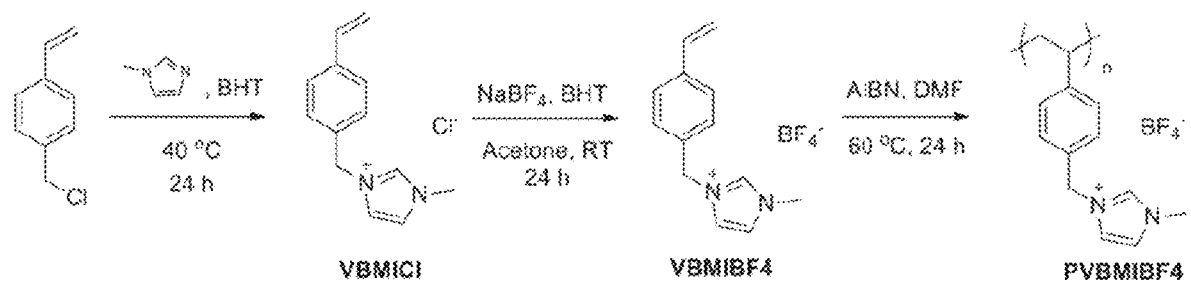
FIG. 1 illustrates synthesis of the imidazolium-based PIL (poly(ionic liquid)), PVBMIBF4.

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

This disclosure provides another class of sensor, chemiresistive sensors, which have significant promise for low-cost and low-power sensing. It should be noted that polyethylenimine (PEI) and polyethylene glycol (PEG) in a combined polymer system have shown promise in $CO_2$ sensitive chemiresistive devices, when used in conjunction with graphene. Furthermore, ionic liquids have been shown to absorb significant quantities of $CO_2$, due to the affinity of $CO_2$ towards many of the ionic moieties contained within, and thus provide potential utility for increasing the $CO_2$ uptake of chemiresistive sensors. In order to leverage both of these advantages in combination, devices were fabricated on a printed circuit board with a PEI-PEG-PIL ink on top of a carbon nanotube (CNT) film. This CNT film bridged gold-plated electrode pairs created via low-cost commercial printed circuit board (PCB) fabrication processes. These devices enable sensitivity to $CO_2$ within the ppm ranges relevant for indoor occupancy monitoring and related applications. The experimental methods employed herein are described in the Material Development, Device Fabrication, and Experimental Testing sections, while the corresponding results and interpretation are presented in the Results and Discussion section.

In one embodiment, the present disclosure provides a composite film configured for $CO_2$ sensing, wherein the composite film comprises a carbon nanotube film and a $CO_2$ absorbing layer deposited on the carbon nanotube film, wherein the $CO_2$ absorbing layer comprises a mixture of a branched polyethylenimine, a polyethylene glycol, and poly[1-(4-vinylbenzyl)-3-methylimidazolium tetrafluoroborate] (PVBMIBF4) of formula I:

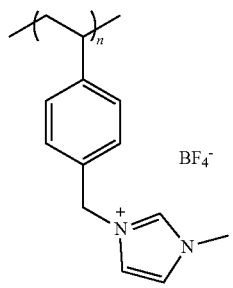

I wherein n ranges from 10-300

In one embodiment regarding the composite film configured for $CO_2$ sensing, wherein the thickness of said carbon nanotube film is about 10-500 nm, 10-400 nm, 10-300 nm, 10-200 nm, or 10-100 nm. The thickness of said $CO_2$ absorbing layer is 100-1000 nm, 100-900 nm, 100-800 nm, 100-700 nm, 100-600 nm, 100-500 nm. In one aspect, the thickness of said carbon nanotube film is about 100 nm, the thickness of said $CO_2$ absorbing layer is about 500 nm.

In one embodiment regarding the composite film configured for $CO_2$ sensing, wherein said carbon nanotube film comprises chlorosulfonic acid.

In one embodiment regarding the composite film configured for $CO_2$ sensing, wherein said branched polyethylenimine has a molar molecular weight of about 1.0-20, 1.0-10, 5-20, 5-10 kg/mol, wherein said branched polyethylene glycol has a molar molecular weight of about 0.5 kg/mol to 50, 0.5 kg/mol to 40, 0.5 kg/mol to 30 kg/mol.

In one embodiment regarding the composite film configured for $CO_2$ sensing, wherein said branched polyethylenimine has a weight percentage of 40-60% of the total weight of the $CO_2$ absorbing layer.

In one embodiment regarding the composite film configured for $CO_2$ sensing, wherein said polyethylene glycol has a weight percentage of 40-60% of the total weight of the $CO_2$ absorbing layer.

In one embodiment regarding the composite film configured for $CO_2$ sensing, wherein said poly[1-(4-vinylbenzyl)-3-methylimidazolium tetrafluoroborate] has a weight percentage of about 1-10, 1-5, 1-3% of the total weight of the $CO_2$ absorbing layer. In one aspect, said poly[1-(4-vinylbenzyl)-3-methylimidazolium tetrafluoroborate] has a weight percentage of about 1-3% of the total weight of the $CO_2$ absorbing layer.

Material Development

Material Sourcing

CoMoCAT™ Signis SG65i semiconducting single wall carbon nanotubes (CNTs), chlorosulfonic acid, poly(ethylene glycol) (PEG, Mn=300 g mol-1) and branched poly(ethylenimine) (PEI, Mn=10,000 g mol-1) were purchased from Sigma-Aldrich, and the materials were used as received. Poly(4-vinylbenzyltrimethylammonium tetrafluoroborate) (PVBMIBF$_4$) was synthesized according to a previous report [See J. Tang, H. Tang, W. Sun, M. Radosz, and Y. Shen, "Poly(ionic liquid)s as new materials for $CO_2$ absorption," *Journal of Polymer Science Part A: Polymer Chemistry*, vol. 43, no. 22, pp. 5477-5489, 2005]. The reaction scheme is shown in FIG. 1.

We utilized a mixture of branched PEI and PEG as the $CO_2$ absorbing layer. PEI, a highly branched polymer with a rich amount of secondary and tertiary amino groups along the polymer backbone, n-dopes the carbon nanotubes with its electron negative lone pairs. Upon exposure to $CO_2$, the amino groups readily react to form electron deficient ammonium cations, and the n-doping effect is hence weakened, which leads to the change in the carrier concentration within the CNTs. Because this reaction is facilitated by water, PEG is used as a vapor absorbing material, which holds water molecules in this layer.

Device Fabrication

Preparation and Transfer of CNT Thin Films

Figure 2:
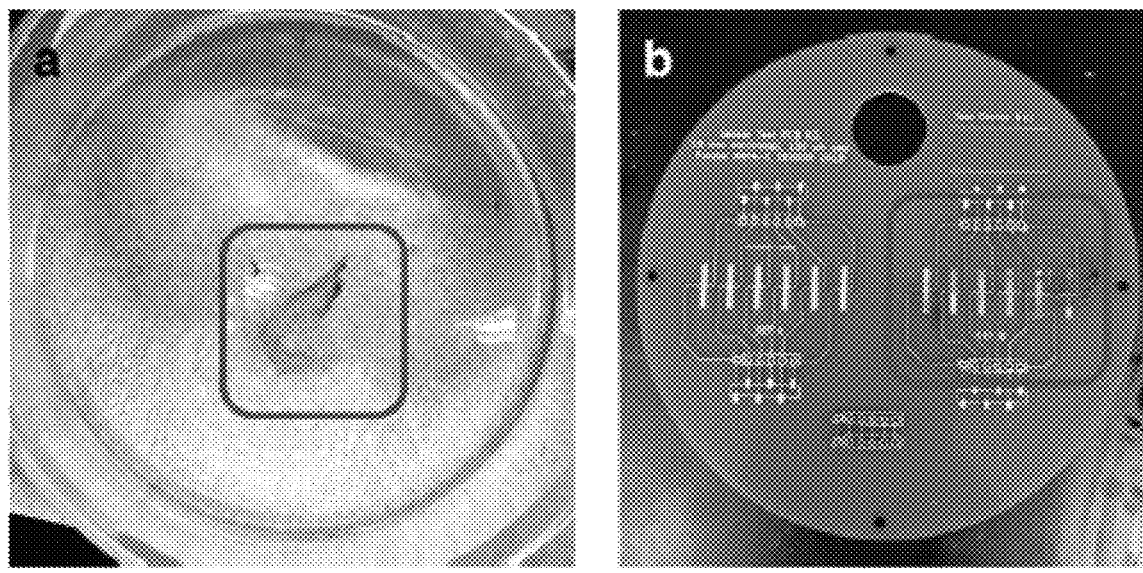
FIG. 2 illustrates (a) free-floating CNT film generated after casting a dispersion of the CNTs from a concentrated solution. The CNT film floating on water is highlighted by the red box. (b) The final CNT thin films after they have been laminated atop the pre-fabricated PCB substrates. The devices with the CNT thin films laminated on them are highlighted by the blue box. A separate set of bare electrodes are available but are intentionally not covered with CNTs for visual demonstration purposes.

About 3 mg of CNTs were added to 3 mL of chlorosulfonic acid. The mixture was allowed to stir under inert condition for 3 days to form a thick solution of CNTs. 20 μL of solution was sandwiched between two glass slides, and the thin film was generated by manually pressing and sliding, in a manner similar to what has been reported previously. To transfer the thin film, a glass slide was gently placed into water to peel off the thin film, and the free-floating film [see FIG. 2(a)] was deposited onto a PCB substrate between pre-patterned electrodes [see FIG. 2(b)].

Preparation of the CNT-PEI-PEG-PIL Devices

About 0.2 g of PEI and 0.6 g of PEG were dissolved in 20 g of methanol to generate a solution of 1% of PEI and 3% of PEG (Solution A). 10 mg of the PIL was dissolved in 1 g of acetonitrile to give a solution of 1% of PIL (Solution B). Then, 100 μL of Solution A and 10 μL of Solution B were mixed and diluted by methanol to a total volume of 1 mL to generate a solution of 0.1% of PEI, 0.3% of PEG and 0.01% of PIL (Solution C). The $CO_2$ sensors were fabricated by drop-casting Solution C onto the CNT thin films over the PCB substrates, followed by the removal of methanol by drying for 5 hr.

Testing Procedure

Figure 3:
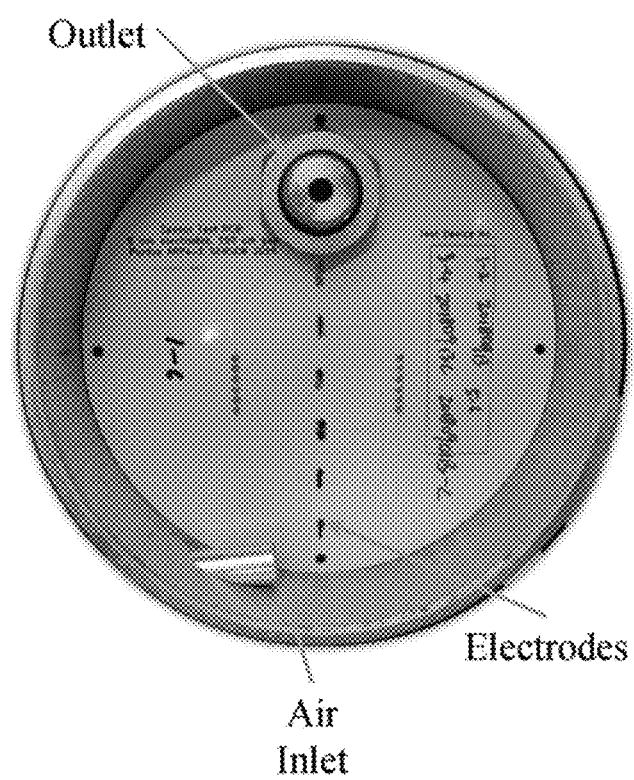
FIG. 3 illustrates sensing chamber with six chemiresistive sensors.

The testing chamber, as seen in FIG. 3, was a 114 mm diameter and 20 mm tall cylindrical chamber. The walls of the chamber were aluminum. The base was a fiberglass printed circuit board (PCB) with the sensors integrated therein and the top was a glass window for observation. The 9.5 mm diameter air inlet was located on the aluminum wall, and the 9.5 mm diameter air outlet was fixed to the PCB base. The chamber was supplied with gas via an inline flow distribution system with two gas sources: pure nitrogen and a mixture of 1% carbon dioxide and 99% nitrogen. The gas sources were connected to three mass flow controllers (MFC) in parallel. The nitrogen carrier gas was controlled through two 50 ccm rated MFCs (MKS Instruments 1179C) while the carbon dioxide and nitrogen mixed gas was controlled through a 10 ccm rated MFC (Unit Instruments UFC-1661, 10 ccm). These inlets were connected to a manifold, the output of which was connected directly to the chamber inlet.

Immediately prior to testing, the PCB substrate was secured and the chamber was sealed. The chamber was flushed with pure nitrogen at 500 ccm to create an inert environment as a baseline reference. Carbon dioxide was then introduced to the chamber at prescribed concentrations, alternated with nitrogen every 40 min, while maintaining the overall volumetric flow rate constant at 500 ccm for each concentration change. The resistances of the electrode pairs were measured using benchtop digital multimeters (Keysight 34401A) over time (sampling rate of 0.5 Hz) and the MFCs were controlled via a custom breakout board connected to an Agilent Technologies U2781A USB module DAQ chassis containing U2541A modular USB data acquisition modules, which provided analog input and output. The control of the MFCs and sampling from the multimeters was facilitated with a National Instruments LabVIEW virtual instrument program.

Results and Discussion

Figure 4:
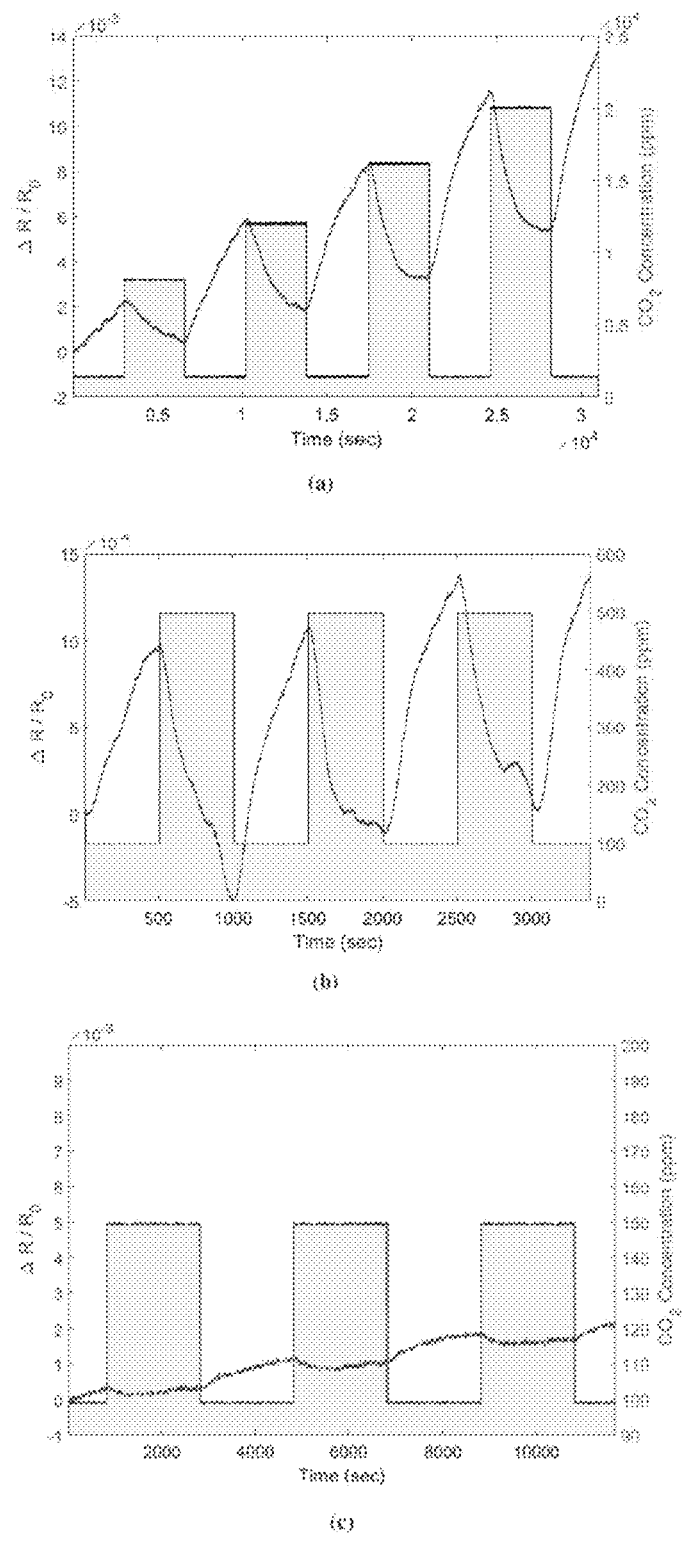
FIG. 4 illustrates measured change in sample resistance to (a) 8,000-20,000 ppm (b) 500 ppm, and (c) 50 ppm $CO_2$ pulses with a background of 100 ppm $CO_2$ in $N_2$ with 40% relative humidity at room temperature.

A discernible response signal was first obtained by measuring the resistance across each sensor with a benchtop digital multimeter. The relative response shift was then calculated as:

$$\frac{\Delta R}{R_0} = \frac{R - R_0}{R_0}, \quad (1)$$

where R is the measured electrical resistance, in Ohms, and $R_0$ is the electrical resistance at the beginning of the test. Multiple representative tests are shown in FIG. 4 where the relative resistance response (line) is shown against the exposed $CO_2$ concentration (shaded regions). FIG. 4(a) shows the sensor response to high concentrations of $CO_2$ in ranges relevant to industrial applications and human respiration monitoring. FIG. 4(b) and FIG. 4(c) show sensor response in ranges relevant to indoor air quality monitoring and occupancy monitoring.

NDIR-type sensors are the most common commercially available $CO_2$ sensors given their accuracy at a relatively low cost. An accuracy of ±20 ppm was established for some commercially available NDIR $CO_2$ sensors in the sub 50,000 ppm range [See S. K. Pandey and K.-H. Kim, "The relative performance of NDIR-based sensors in the near real-time analysis of $CO_2$ in air," Sensors, vol. 7, no. 9, pp. 1683-1696, 2007]. In another analysis of the performance of commercial NDIR $CO_2$ sensors [See T. Yasuda, S. Yonemura, and A. Tani, "Comparison of the characteristics of small commercial NDIR $CO_2$ sensor models and development of a portable $CO_2$ measurement device," Sensors, vol. 12, no. 3, pp. 3641-3655, 2012], NDIR sensors with an accuracy of ±30 ppm were evaluated. These sensors were shown to be able to respond to small changes (less than 100 ppm) in $CO_2$ concentration around room limits (e.g., under 1000 ppm). The chemiresistive sensors tested here exhibit clear response deviations in the presence of 50 ppm of $CO_2$ on a 100 ppm background, which is comparable to their commercial NDIR counterparts. Accordingly, the examined device shows promise as a $CO_2$ sensor that can sense the gas at a lower cost, and with lower power, than traditional detection methods.

While the relative changes in resistances are small in an absolute sense, the qualitative signal-to-noise ratio appears sufficient to discern the measurement trends and measure changes in $CO_2$ concentration across a wide range. Wheatstone bridge circuits or other techniques could be economically used in order to amplify this response for use in a sensing system. Drift appears to be an issue with this device, and characterization of this behavior, as well as the device's sensitivity to distractant vapors, humidity, and temperature are an area of ongoing research. Additional avenues for response optimization include tuning the geometry of the device electrodes and improving the CNT and polymer deposition steps for increased consistency and reliability so that the effect of film thicknesses can be better studied.

This work demonstrated that fabricated chemiresistive devices, comprised of a PEI-PEG-PIL and CNT combination, successfully sensed changes in $CO_2$ concentration. It was found that the change in resistance from an initial value was a monotonic function of the $CO_2$ concentration in the surrounding environment. Given the relatively low cost and their potential for low power consumption, these chemiresistive sensors serve as an attractive alternative to current commercially available $CO_2$ sensors.

We claim:

1. A composite film configured for $CO_2$ sensing, wherein the composite film comprises a carbon nanotube film and a $CO_2$ absorbing layer deposited on the carbon nanotube film, wherein the $CO_2$ absorbing layer comprises a mixture of a branched polyethylenimine, a polyethylene glycol, and poly[1-(4-vinylbenzyl)-3-methylimidazolium tetrafluoroborate] of formula I:

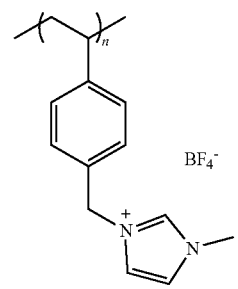

I wherein n ranges from 10-300.

2. The composite film of claim 1, wherein the thickness of said carbon nanotube film is 10-500 nm, the thickness of said $CO_2$ absorbing layer is 100-1000 nm.

3. The composite film of claim 1, wherein said carbon nanotube film comprises chlorosulfonic acid.

4. The composite film of claim 1, wherein said branched polyethylenimine has a molar molecular weight of 10 kg/mol, wherein said polyethylene glycol has a molar molecular weight of 0.5 kg/mol to 50 kg/mol.

5. The composite film of claim 1, wherein said branched polyethylenimine has a weight percentage of 40-60% of the total weight of the $CO_2$ absorbing layer.

6. The composite film of claim 1, wherein said polyethylene glycol has a weight percentage of 40-60% of the total weight of the $CO_2$ absorbing layer.

7. The composite film of claim 1, wherein said poly[1-(4-vinylbenzyl)-3-methylimidazolium tetrafluoroborate] has a weight percentage of 1-5% of the total weight of the $CO_2$ absorbing layer.

* * * * *